US009588095B2

(12) United States Patent
Gregory et al.

(10) Patent No.: US 9,588,095 B2
(45) Date of Patent: Mar. 7, 2017

(54) REAGENTS FOR OXIDIZER-BASED CHEMICAL DETECTION

(71) Applicant: Massachusetts Institute of Technology, Cambridge, MA (US)

(72) Inventors: Kerin E. Gregory, Bolton, MA (US); Roderick R. Kunz, Acton, MA (US); Michael Sworin, Marlboro, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 390 days.

(21) Appl. No.: 13/948,423

(22) Filed: Jul. 23, 2013

(65) Prior Publication Data
US 2015/0004710 A1    Jan. 1, 2015

Related U.S. Application Data

(63) Continuation-in-part of application No. 13/832,905, filed on Mar. 15, 2013.
(Continued)

(51) Int. Cl.
*G01N 33/22* (2006.01)
*G01N 27/62* (2006.01)
(Continued)

(52) U.S. Cl.
CPC ......... *G01N 33/227* (2013.01); *G01N 27/622* (2013.01); *G01N 31/227* (2013.01);
(Continued)

(58) Field of Classification Search
CPC .......................... G01N 33/227; G01N 21/622
(Continued)

(56) References Cited

U.S. PATENT DOCUMENTS 4,201,839 A * 5/1980 Johnson ............ H01M 10/0566
                                                429/199
4,752,448 A    6/1988 Wells et al.
(Continued)

FOREIGN PATENT DOCUMENTS

EP    1145005    10/2001
EP    1844189    10/2007
(Continued)

OTHER PUBLICATIONS

Masataka Sakayanagi, Yaeko Yamada, Chikako Sakabe, Kunio Watanabe, Yoshihiro Harigaya "Identification of inorganic anions by gas chromatography/mass spectrometry" Forensic Science International 157 (2006) 134-143.*
(Continued)

*Primary Examiner* — Christine T Mui
*Assistant Examiner* — Emily Berkeley
(74) *Attorney, Agent, or Firm* — Thomas J. Engellenner; Reza Mollaaghababa; Pepper Hamilton

(57) ABSTRACT

Reagents and methods are disclosed for detection of oxidizers and inorganic salts and other analytes of interest. The reagents can interact with their target analytes, especially oxidizer compositions or oxidizer-based explosives, to selectively enhance their ionization yield, interacting by chemical reaction or by forming an associative adduct which facilitates their detection. For example, the reagents can adduct with the counter-ion of the intended analyte for improved direct detection and/or react chemically via acid-base reactions to produce a new product for detection. In another aspect of the invention, reactive reagents and methods are also disclosed that facilitate indirect detection of the analyte at lower temperatures based on reduction-oxidation (redox) chemistry. These reagents are particularly useful in detecting oxidizer analytes.

20 Claims, 8 Drawing Sheets

Related U.S. Application Data

(60) Provisional application No. 61/674,980, filed on Jul. 24, 2012, provisional application No. 61/806,636, filed on Mar. 29, 2013.

(51) Int. Cl.
*G01N 31/22* (2006.01)
*G01N 1/02* (2006.01)

(52) U.S. Cl.
CPC .................. *G01N 2001/028* (2013.01); *Y10T 436/141111* (2015.01); *Y10T 436/143333* (2015.01); *Y10T 436/173076* (2015.01); *Y10T 436/19* (2015.01); *Y10T 436/206664* (2015.01); *Y10T 436/24* (2015.01)

(58) Field of Classification Search
USPC ......................................................... 436/169
See application file for complete search history.

(56) References Cited

U.S. PATENT DOCUMENTS

| | | | |
|---|---|---|---|
| 5,988,002 | A | 11/1999 | Danylewych-May et al. |
| 6,287,780 | B1 | 9/2001 | Schmidt et al. |
| 6,627,444 | B1 | 9/2003 | Goledzinowski et al. |
| 7,439,496 | B2 | 10/2008 | Stott et al. |
| 8,119,984 | B2 | 2/2012 | Shabanowitz et al. |
| 8,304,251 | B2 | 11/2012 | Haas et al. |
| 2004/0157344 | A1 | 8/2004 | Wang et al. |
| 2005/0288616 | A1* | 12/2005 | Bozenbury, Jr. ......... G01N 1/02 604/1 |
| 2006/0192098 | A1 | 8/2006 | Danylewych-May et al. |
| 2008/0245963 | A1 | 10/2008 | Land et al. |
| 2009/0032701 | A1 | 2/2009 | Rodier et al. |
| 2009/0039243 | A1 | 2/2009 | Wynn et al. |
| 2009/0078862 | A1 | 3/2009 | Rodier et al. |
| 2010/0047849 | A1 | 2/2010 | Caulfield et al. |
| 2010/0291704 | A1 | 11/2010 | Cody |
| 2012/0181421 | A1* | 7/2012 | Satoh .................... H01J 49/142 250/282 |

FOREIGN PATENT DOCUMENTS

| | | |
|---|---|---|
| WO | 9905319 A2 | 2/1999 |
| WO | 2007066240 | 6/2007 |

OTHER PUBLICATIONS

Yongtao Li, Joshua S. Whitaker, Christina L. McCarty "Reversed-phase liquid chromatography/electrospray ionization/mass spectrometry with isotope dilution for the analysis of nitrate and nitrite in water" Journal of Chromatography A, 1218 (2011) 476-483.*

PCT International Preliminary Report on Patentability and PCT Written Opinion of the International Searching Authority for PCT/US2013/051676, mailed Jan. 27, 2015 (8 pages.).

PCT Notification of Transmittal of the International Search Report and the Written Opinion of the International Searching Authority, or the Declaration, PCT/US2013/051676, mailed May 27, 2014 (11 pages.).

U.S. Appl. No. 13/832,905, filed Mar. 15, 2013, Reagent Impregnated Swipe for Chemical Detection.

PCT/US13/51671, Jul. 23, 2013, Reagent Impregnated Swipe for Chemical Detection.

PCT/US13/51676, Jul. 23, 2013, Reagents for Oxidizer-Based Chemical Detection.

Brodbelt, J. S.; Liou, C. C., New frontiers in host-guest chemistry—the gas phase. Pure and Applied Chemistry 1993, 65 (3), 409-414.

Chu, I. H.; Zhang, H.; Dearden, D. V., Macrocyclic chemistry in the gas phase—intrinsic cation affinities and complexation rates for alkali-metal cation complexes of crown-ethers and glymes. Journal of the American Chemical Society 1993, 115 (13), 5736-5744.

De Perre, C.; Prado, A.; McCord, B. R., Rapid and specific detection of urea nitrate and ammonium nitrate by electrospray ionization time-of-flight mass spectrometry using infusion with crown ethers. Rapid Communications in Mass Spectrometry 2012, 26 (2), 154-162.

Dietrich, B.; Kintzinger, J. P.; Lehn, J. M.; Metz, B.; Zahidi, A., Stability, molecular-dynamics in solution, and x-ray structure of the ammonium cryptate NH4+ subset of 2.2.2.PF6. Journal of Physical Chemistry 1987, 91 (27), 6600-6606.

Eiceman, G. A.; Yuan-Feng, W.; Garcia-Gonzalez, L.; Harden, C. S.; Shoff, D. B., Enhanced selectivity in ion mobility spectrometry analysis of complex mixtures by alternate reagent gas chemistry. Analytica Chimica Acta 1995, 306 (1), 21-33.

Evans, C. S.; Sleeman, R.; Luke, J.; Keely, B. J., A rapid and efficient mass spectrometric method for the analysis of explosives. Rapid Communications in Mass Spectrometry 2002, 16 (19), 1883-1891.

Ewing, R. G.; Atkinson, D. A.; Eiceman, G. A.; Ewing, G. J., A critical review of ion mobility spectrometry for the detection of explosives and explosive compounds. Talanta 2001, 54 (3), 515-529.

Flanigan, P. M.; Brady, J. J.; Judge, E. J.; Levis, R. J., Determination of Inorganic Improvised Explosive Device Signatures Using Laser Electrospray Mass Spectrometry Detection with Offline Classification. Analytical Chemistry 2011, 83 (18), 7115-7122.

Graf, E.; Kintzinger, J. P.; Lehn, J. M.; Lemoigne, J. Molecular recognition—selective ammonium cryptates of synthetic receptor molecules possessing a tetrahedral recognition site. Journal of the American Chemical Society 1982, 104 (6), 1672-1678.

Kozole, J.; Tomlinson-Phillips, J.; Stairs, J. R.; Harper, J. D.; Lukow, S. R.; Lareau, R. T.; Boudries, H.; Lai, H.; Brauer, C. S., Characterizating the gas phase ion chemistry of an ion trap mobility spectrometry based explosive trace detector using a tandem mass spectrometer. Talanta 2012, 99, 799-810.

Lawrence, A. H.; Neudorfl, P., Detection of ethylene glycol dinitrate vapors by ion mobility spectrometry using chloride reagent ions. Analytical Chemistry 1988, 60 (2), 104-109.

Maleknia, S.; Brodbelt, J., Cavity-size-dependent dissociation of crown-ether ammonium ion complexes in the gas-phase. Journal of the American Chemical Society 1993, 115 (7), 2837-2843.

More, M. B.; Ray, D.; Armentrout, P. B., Intrinsic affinities of alkali cations for 15-crown-5 and 18-crown-6: Bond dissociation energies of gas-phase M+-crown ether complexes. Journal of the American Chemical Society 1999, 121 (2), 417-423.

Park, K.-M.; Kim, H. J.; Moon, S.-H.; Vittal, J. J.; Jung, J. H.; Lee, S. S., Surprisingly stable ammonium ion complex of a non-cyclic crown-type polyether: Solid and solution studies. New Journal of Chemistry 2010, 34 (4), 603-606.

Sassine, A.; Martins-Junior, H. A.; Lebre, D. T.; Valli, F.; Pires, M. A. F.; Vega, O.; Felinto, M. C. F. C., An electrospray ionization tandem mass spectrometric study of p-tert-butylcalix[6]arene complexation with ammonium hydroxide, and ammonium and sodium ions. Rapid Communications in Mass Spectrometry 2008, 22 (3), 385-393.

Späth, A.; Koenig, B., Molecular recognition of organic ammonium ions in solution using synthetic receptors. Beilstein Journal of Organic Chemistry 2010, 6.

Taylor, V. F.; March, R. E.; Longerich, H. P.; Stadey, C. J., A mass spectrometric study of glucose, sucrose, and fructose using an inductively coupled plasma and electrospray ionization. International Journal of Mass Spectrometry 2005, 243 (1), 71-84.

Tsai, C.-W.; Midey, A.; Wu, C.; Yost, R. A. Analysis of ammonium nitrate/urea nitrate with crown ether and sugar as modifiers, American Society for Mass Spectrometry, Denver, 2011.

Badu-Tawiah, A. K.; Campbell, D. I.; Cooks, R. G., Reactions of microsolvated organic compounds at ambient surfaces: Droplet velocity, charge state, and solvent effects. Journal of the American Society for Mass Spectrometry 2012, 23 (6), 1077-1084.

Benassi, M.; Wu, C.; Nefliu, M.; Ifa, D. R.; Volny, M.; Cooks, R. G., Redox transformations in desorption electrospray ionization. International Hournal of Mass Spectrometry 2009, 280, 325-240.

Fieser, M., Fiesers' Reagents for Organic Synthesis, vol. 27, John Wiley & Sons, 2011. Table of contents.

(56) References Cited

OTHER PUBLICATIONS

McDougall, J.L.; Simkins, R.J.J., The identification of traces of explosives by field spot tests in Ministry of Defense Explosives Research and Development Establishment, Technical Report No. 122, Mar. 1973.

Smith, M., March's Advanced Organic Chemistry: Reactions, Mechanisms and Structure, 7th Edition, Wiley & Sons, 2013. Table of contents.

Sundberg, R. J.; Carey, F. A., Advanced Organic Chemistry, Part B: Reactions and Synthesis, 5th Edition, Springer, 2007. Table of contents.

Urbansky, E.T.; Magnuson, M.L.; Freeman, D.; Jelks, C., Quantitation of perchlorate ion by electrospray ionization mass spectrometry (ESI-MS) using stable association complexes with organic cations and bases to enhance selectivity, Journal of Analytical Atomic Spectrometry 1999, 14, 1861-1866.

* cited by examiner

Scheme 1 (Associative Reagent):
Reagent A⁻ preferentially ligates counter-ion allowing M⁻ to be more readily detected directly $$MX + A^- \rightarrow M^- + XA$$

Scheme 2 (Acid-Base Reactive Reagent):
Acid reagent serving as a proton donor H⁺ forming acid of M, represented as HM, a volatile species which ionizes readily for detection $$MX + H^+ \rightarrow HM + X^+$$

Scheme 3 (Co-reagent system using schemes 1 and 2):
Two reagent system combining acid reagent H⁺ to form acidic analog of analyte combined with counter-ion associative reagent A. Volatile product HM is formed which ionizes readily for detection $$MX + H^+ + A^- \rightarrow HM + XA$$

Also, optional additional adduct reagent R to shift to higher mass or provide MS/MS fragmentation precursor, by
$HM + R \rightarrow RM^- + H^+$ (or $R(HM)_nM^- + H^+$, where n=number of HM units in cluster)

FIG. 1

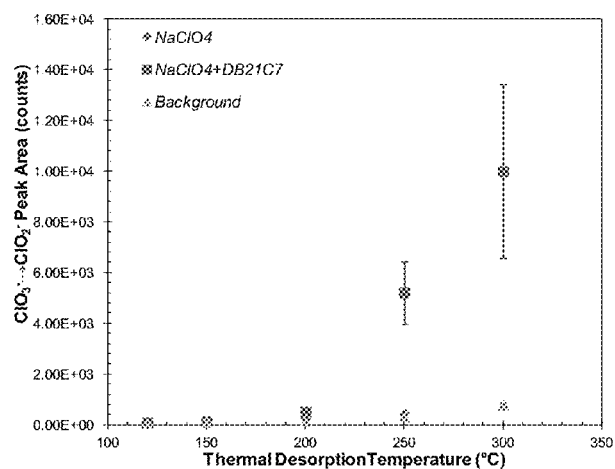
FIG. 8
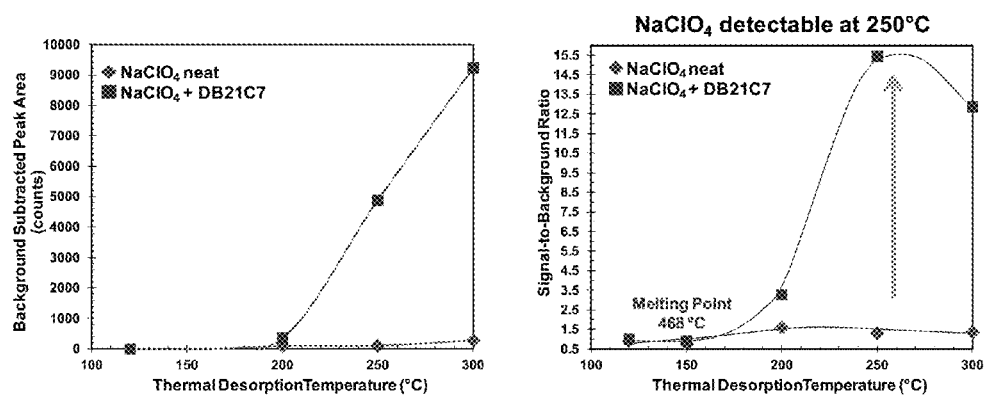
FIG. 9
FIG. 10

REAGENTS FOR OXIDIZER-BASED CHEMICAL DETECTION

REFERENCE TO RELATED APPLICATIONS

This application claims the benefit of, and priority to, U.S. Provisional Patent Application No. 61/674,980 filed Jul. 24, 2012 and U.S. Provisional Patent Application No. 61/806,636, filed Mar. 29, 2013.

This application is also a continuation-in-part of U.S. patent application Ser. No. 13/832,905 filed Mar. 15, 2013.

GOVERNMENT RIGHTS

This invention was made with U.S. government support under Interagency Agreements HSHQDC-09-X-00439 and HSHQPM-12-X-00057 by the U.S. Department of Homeland Security, Science and Technology Directorate, and performed by MIT Lincoln Laboratory under Air Force Contract No. FA8721-05-C-0002. The U.S. government has certain rights in the invention.

The contents of each of the above-referenced related application are herein incorporated by reference in its entirety.

FIELD OF THE INVENTION

The present invention concerns contraband detection and, in particular, novel reagents for spectrometric detection of oxidizer-based explosives in ambient pressure ionization detectors and the like.

BACKGROUND OF THE INVENTION

The evolving threats posed by concealed explosives or the intentional release of toxic chemicals demand new ways to detect these threats and protect the public. Typically, the techniques for identifying threat molecules involve ionizing a sample and then detecting whether the threat molecule (analyte) is present. The detection mechanisms include ion mobility spectrometry (IMS), differential mobility spectrometry (DMS), field asymmetric ion mobility spectrometry (FAIMS), and mass spectrometry (MS), all of which rely upon ionization of the analyte or a complex that includes the analyte. In fact, one of these techniques (IMS) is currently used in nearly every airport in the United States as a means to prevent concealed explosives from getting on aircraft.

Given the importance of these techniques to public safety, considerable effort has been devoted to develop better techniques for efficiently (and selectively) ionizing analytes in order to provide the greatest detection capability.

In almost all instances, ionization is achieved selectively by performing the ionization under ambient-pressure conditions in the presence of an ionization reagent in a technique known as ambient-pressure ionization (API) (also sometimes called atmospheric-pressure chemical ionization). In API, the target analyte is drawn into a space containing both an ionization source and an ionization reagent, and ionization of the target molecule takes place through ion-molecule collisions. The ionization reagent is selected such that rapid achievement of charge equilibrium results in charge or proton transfer from the reagent to the target molecule.

Since many explosive and chemical threats have low vapor pressure and exist as traces of particulates or thin films on surfaces, the most common way to collect a sample requires a swipe or swab substrate which provides a physical mechanism to both collect and preconcentrate a sample taken from a surface of a suspect object for subsequent presentation to the ionization space of the detection instrument. The substrate media, which is called a "swipe," can be thermally heated to desorb the target analyte into the vapor phase for subsequent ionization and detection. This methodology is currently used in fielded IMS systems that detect explosives, where detection relies on efficient collection and presentation of low-vapor analytes such as 2,4,6-trinitrotoluene (TNT), 1,3,5-trinitro-1,3,5-triazacyclohexane (RDX) and pentaerythritol tetranitrate (PETN) into the instrument, and use of ionization reagents that enhance the formation of negative ions via chloride adduction, such as methylene chloride.

In such explosive detection systems, the swipe or substrate is typically positioned in a thermal desorber located on the inlet side of the detection system. Thermal heating of the solid particles on the swipe induces a solid-to-vapor phase transition and releases the analyte molecules as a vapor, usually guided into the sensor inlet by a carrier gas, and the ionization reagent is introduced as a vapor within a separate carrier gas. Properties of commercially-available swipe media have been optimized over the years for increased efficiency of particle collection from surfaces (mechanical or electrostatic), efficient transfer and release of analyte into the chemical sensor, thermal stability, and low chemical background of the substrate.

Detection of both inorganic and organic oxidizer-based explosives can be a particularly difficult problem. Some examples of inorganic oxidizer-based explosives include perchlorate ($KClO_4$, $NaClO_4$), chlorate ($KClO_3$, $NaClO_3$), and nitrate ($NH_4NO_3$, $KNO_3$, $NaNO_3$) salts and hydrogen peroxide ($H_2O_2$). Examples of organic oxidizer-based explosives are hexamethylene triperoxide diamine (HMTD), triacetonetriperoxide (TATP), and diacetonediperoxide (DADP). Inorganic oxidizers, generally speaking, are chemical compositions that contribute oxygen in which the fuel component of an explosive can burn. Two factors that contribute to the difficulty in detecting inorganic oxidizers are their low vapor pressure and low ionization yield. Low volatility analytes require high thermal desorption and/or ionization source temperatures. (In some cases the temperature necessary to transform oxidizer analytes into their vapor phase can exceed 350° C.—a regime in which common swipe materials cannot be used.) Achieving high temperature is an engineering challenge specifically in smaller, field portable systems where size, weight and power must be minimized and long thermal cycling reduces sample throughput. Even when ionized, this class of analytes are often prone to quickly recombine into neutral species before they can be subjected to spectrometric analysis. Moreover, some of the analytes also form ubiquitous, non-specific products upon thermal desorption, e.g. nitrate from ammonium nitrate, potassium nitrate, and sodium nitrate.

Accordingly, there exists a need for better methods and reagents for detecting oxidizer compositions and oxidizer-based explosives. Reagents that can improve desorption (release of analytes from a substrate), increase the quantity or longevity of ionized analyte species or otherwise improve the detector efficiency would satisfy a long-feel need in the field. Additionally, indirect techniques for detecting or quantifying oxidizer analytes based on formation of complexes or chemical modification of reagents, which can be more readily detected, would also provide an improvement in the art.

SUMMARY OF THE INVENTION

Reagents and methods are disclosed for detection of both inorganic and organic oxidizers, inorganic salts and other analytes of interest. The reagents can interact with their target analytes, especially oxidizer compositions or oxidizer-based explosives, to selectively enhance their ionization yield, interacting by chemical reaction or by forming an associative adduct which facilitates their detection. For example, the reagents can adduct with the counter-ion of the intended analyte for improved direct detection of the analyte and/or react chemically via acid-base reactions to produce a new product for detection. Reactive reagents and methods are also disclosed that facilitate indirect detection of the analyte at lower temperatures based on reduction-oxidation (redox) chemistry. These reagents are particularly useful in detecting oxidizer analytes, such as salts of nitrates, nitrites, chlorates, perchlorates, permanganates, dichromates or osmium tetraoxide.

In one aspect of the invention, associative reagents are disclosed to improve ionization yield. In some instances, the reagents can also improve yield at lower temperatures than currently necessary to achieve a desired degree of accuracy. In certain embodiments, the reagents serve to sequester one or more ionic species. For example, detection of certain oxidizers, such as potassium perchlorate $KClO_4$, is limited in conventional ambient pressure ionization systems by the ionization yield. Associative reagents are disclosed that can sequester the cation (e.g. $K^+$) from the intended analyte (e.g. $ClO_4^-$ in negative mode ionization) which will increase the availability of the analyte (perchlorate) for direct detection. This premise will also function where a reagent binds the anion leaving the cationic analyte free to be directly detected. In either case, if needed for improving detection, a co-reagent molecule may also be used to adduct to or react with the analyte ion produced in the first interaction.

In another aspect of the invention, evaporative reagents are disclosed to increase the vapor pressure of the analyte or a component thereof. For example, the evaporative reagent can serve as a proton donor and shift the equilibrium in favor of forming the acid of the salt. The acid analog can enhance direct detection of the analyte by increasing vapor pressure and/or improving ionization probability at lower temperatures. The volatile protonated analyte can then be readily ionized for detection. This acid-base equilibrium approach can be exploited as a single reagent system or in tandem with an associative reagent, as needed to enhance detection.

Thus, in yet another aspect of the invention, a two (or multi) reagent system is disclosed combining an evaporative reactant (e.g., a $H^+$ donor to form an acidic analog of the analyte) with a counter-ion associative reagent. The associative reagent will ensure that, following volatilization and ionization, the analyte will not quickly recombine with its counter ion into a neutral species.

In another aspect of the invention, reactive reagents are disclosed that facilitate indirect detection of the analyte at lower temperatures based on reduction-oxidation (redox) chemistry. These reagents are particularly useful in detecting oxidizer analytes. In one embodiment, the redox reagents accept one or more oxygen atoms from oxidizers present in the sample. The oxidized reagent species can then be detected by mass spectrometry and the amount of oxidized reagent detected provides an indirect indication of the presence of an oxidizer in a sample.

The invention can also be used in conjunction with other ionization reagents, such as conventional compositions currently used in spectrometric detection that enhance the ionization of desorbed molecules that are volatized from a sample (or a swipe carrying a sample). Ionization reagents useful in the present invention include, for example, polychlorinated alkanes, alkyl amines, and nicotinamide.

The invention can be practiced in various detection systems and is particularly useful in ambient pressure ionization detectors. In such systems, the substrate is positioned in a thermal desorber located on the inlet side of the detection system. Thermal heating of the solid particles on the swipe induces a solid-to-vapor phase transition and releases the analyte molecules as a vapor, usually guided into the sensor inlet by a carrier gas, and the ionization reagent is introduced as a vapor within a separate carrier gas. Properties of commercially-available swipe media have been optimized over the years for increased efficiency of particle collection from surfaces (mechanical or electrostatic), efficient transfer and release of analyte into the chemical sensor, thermal stability, and low chemical background of the substrate. Prior art exists in the patent literature on different embodiments of sampling swipes (e.g., Smiths Detection, Sampling Swab related patents: US20060192098A1; EP1844189A2; WO2007066240A3). In a previous U.S. patent application No. 61/674,980 entitled "Reagent Impregnated Swipe for Thermal Desorption Release and Chemical Detection with Ambient Ionization Techniques", we disclosed an invention where the reagent is chemically embedded in the swipe material for interaction with the analyte.

The reagents of the present invention can be introduced in any physical state including the gas-phase from a vapor permeation device, as a solid on/in a swipe or other substrate, as a liquid infused via nebulizer, or by other various methods for introduction known to those skilled in the art.

In certain embodiments, the reagents of the present invention are low volatility compounds. For example, the reagents can have vapor pressures less than 1 or $10^{-1}$ or $10^{-2}$ or $10^{-3}$ Torr.

In certain embodiments, the associative reagent is adapted to form a host-guest complex with the analyte or its counter-ion constituent. The associative reagent can include at least one of β-keto esters, crown ethers, glymes, sugars, cryptands, ionic dyes, and cavitands.

In yet another aspect of the invention, the reagents of the present invention can be impregnated or otherwise pre-associated with a swipe or other substrate used to collect a sample for analysis. The swipes can further include a plurality of reagents. The plurality of reagents can be associated with spatially separated portions of the swipe or the plurality of reagents can be uniformly applied to substrate. In certain embodiments, the plurality of reagents having different vaporization temperatures. In other embodiments, the swipe can also include one or more internal standards.

The substrate component of the swipe can be formed from various materials, including least one of paper, fabric, cloth, fibrous matte, gauze, cellulose, cotton, flax, linen, synthetic fibers and blends of such materials. The substrate should be clean, and free of extractables, such dirt, grime, contaminants, incidental materials or fabrication residues. In certain preferred embodiments, the substrate has an extractables content of less than 3% or 2% or 1% or 0.1% or 0.01% during desorption. The substrate is preferably also capable of resisting decomposition at temperatures up to about 300° C.

In another aspect of the invention, methods of detecting a target analyte are disclosed, which can include the steps of ionizing molecules present in a sample; exposing the sample molecules to ionization reagents and/or associative reagents, evaporative reagents or redox reagents and analyzing the ionized molecules to detect the target analyte. The methods can further include forming at least one charged complex of the reagent and a target analyte or its counter-ion; and analyzing at least one of the resulting charged species to detect a target analyte. The methods can further include exposing a proton-donating reagent to the sample molecules to modify the vapor pressure, rate of vaporization or ionization potential of the sample molecules.

The step of analyzing the ionized material can further include detection of the charged analyte, charged complex or reactive product by ion mobility spectrometry, differential mobility spectrometry, field asymmetric spectrometry or mass spectrometry. In one preferred embodiment, the ionized molecules are detected by ion mobility spectrometry. Alternatively, they can be detected by mass spectrometry.

By co-introducing and vaporizing both the target analyte and the reagent into the ionization space of an instrument, the two become in communication with one another resulting in ionization of the analyte for direct detection or an oxidized product for indirect detection. The ionization can result in increased ion yield or form a new chemical product with unique characteristics for detection. Also, if the analyte molecule itself was previously undetectable, use of an associative binding reagent for the counter-ion causing its removal from the analyte ion and/or the formation of the more volatile analog of the analyte can allow detection.

When a reagent of the present invention is incorporated into a swipe, the methods of the present invention can further include employing the swipe to collect a sample, heating the swipe to vaporize the molecules present on the swipe and ionizing the molecules, preferably in some cases under ambient pressure conditions. In certain embodiments, the reagent can be a low volatility compound. The methods can further include employing swipes that include multiple reagents. For example, the swipe can include multiple reagents associated with spatially separated portions of the swipe and the step of ionization can further include heating different portions of the swipe in sequence.

Alternatively, two or more reagents having different vapor pressures can be applied to the substrate and the step of ionizing can further include exposing the swipe to a thermal gradient such that the reagents are released sequentially.

More generally, the invention allows the use of reagents for adduct formation and/or chemical reaction to provide flexibility in detecting a wider range of analytes (or for more selective detection) in samples with current and future API-based technologies. Also, a series of reagents may be utilized by introduction simultaneously or at discrete times and temperatures to induce selective reactions with expected oxidizers (e.g. reagent A for perchlorate, reagent B for chlorate, reagent C for hydrogen peroxide, reagent D for TATP, reagent E for HMTD).

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1 illustrates three schema for employing associative and/or acid-base reactive reagents for direct detection of an oxidizer or inorganic salt MX;

FIG. 8 is a graph of TD-APCI of sodium perchlorate ($NaClO_4$) where the instrument response (peak area) is plotted as a function of thermal desorption APCI source temperature (triplicate measurements) for 5 µg $NaClO_4$ (diamonds), 5 µg $NaClO_4$ with 10 µg dibenzo-21-crown-7 (DB21C7) (squares), and background (clean silicon wafer substrate, triangles);

FIG. 9 shows TD-APCI-MS/MS instrument response vs thermal desorption temperature for sodium perchlorate ($NaClO_4$) with and without dibenzo-21-crown-7 (DB21C7) reagent rendered as background-subtracted signal intensity determined using data in FIG. 8, comparing 5 µg $NaClO_4$ (diamonds) and 5 μg NaClO₄ with 10 μg dibenzo-21-crown-7 (DB21C7) (squares), where background is a clean silicon wafer substrate;

FIG. 10 shows TD-APCI-MS/MS instrument response vs thermal desorption temperature for sodium perchlorate (NaClO₄) with and without dibenzo-21-crown-7 (DB21C7) reagent rendered as signal-to-background ratio determined using data in FIG. 8, comparing 5 μg NaClO₄ (diamonds) and 5 μg NaClO₄ with 10 μg dibenzo-21-crown-7 (DB21C7) (squares), where background is a clean silicon wafer substrate;

FIG. 13 illustrates reactive reducing reagent chemistries including redox reactions between classes of carbon, phosphorous, sulfur and nitrogen based compounds and oxidizers. Here, one or more new products are generated for indirect detection of the oxidizing analyte. In these structures, R1, R2, and R3 can be alkyls, lower alkyls, substituted alkyls, substituted lower alkyls, aryls, or substituted aryls such that their vapor pressures are at least 0.001 Torr at 25° C.;

DETAILED DESCRIPTION OF THE INVENTION

Figure 2:
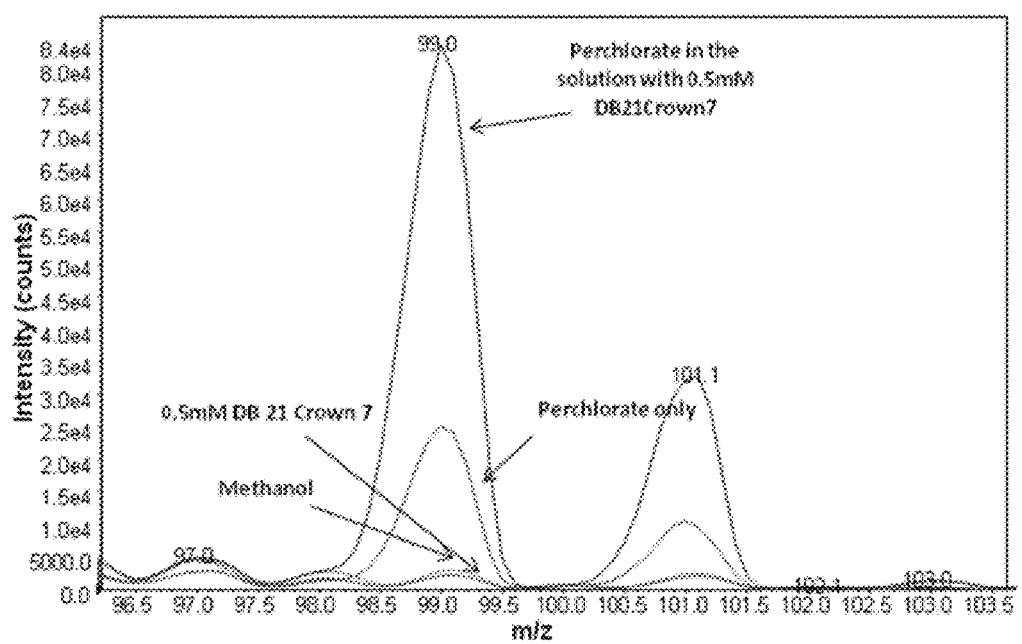
FIG. 2 is a single quadrupole negative-mode mass spectra showing reduction to practice for use of an associative reagent (dibenzo 21-crown-7) to preferentially sequester the potassium counter-ion of potassium perchlorate to increase the available perchlorate anion (m/z 99 for $^{35}ClO_4^-$ and m/z 101 for $^{37}ClO_4^-$) for ionization. The detection sensitivity increased by a factor of 10 using the associative reagent.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Mass spectrometry is an analytical process for identifying a compound or compounds in a sample by assessing the molecular weight, chemical composition and structural information based on the mass-to-charge ratio of charged particles. Mass spectrometry is widely considered to have the best specificity of any technique applicable to a broad class of explosive compounds. In general, a sample undergoes ionization to form charged particles as ions; these charged particles are then passed through electric and/or magnetic fields to separate them according to their mass-to-charge ratio. The terms "mass spectrometry" and "spectrometry" are used herein to encompass techniques that produce a spectrum or spectra of the masses of molecules present in a sample. Mass spectrometry includes, but is not limited to, ion mobility spectrometry (IMS), differential mobility spectrometry (DMS), field asymmetric ion mobility spectrometry (FAIMS), and mass spectrometry (MS), all of which rely upon ionization of the analyte or a complex that includes the analyte. The analysis performed in spectrometry is typically referred to as "mass/charge" analysis, a method of characterizing the ions detected by a spectrometer in terms of their mass-to-charge ratio. The abbreviation m/z is used to denote the dimensionless quantity formed by dividing the mass number of an ion by its charge number. It has long been called the mass-to-charge ratio although m is not the ionic mass nor is z a multiple or the elementary (electronic) charge, e. Thus, for example, for the ion $C_7H_7^{2+}$, m/z equals 45.5.

The ionization process can be performed by a wide variety of techniques, depending on the phase (solid, liquid, gas) of the sample and the efficiency of the target analyte(s) in question. Some examples of ion sources can include electron ionization, glow discharge ionization, resonant ionization, field desorption, fast atom bombardment, thermospray, desorption/ionization on silicon, atmospheric pressure chemical ionization, spark ionization, inductively coupled plasma ionization, secondary ionization by sputtering ion beams off the target's surface, and thermal ionization.

Ambient-pressure ionization, collision-induced ionization, and atmospheric-pressure chemical ionization refer to a characterization techniques in which picogram to microgram quantities of an analyte can be analyzed. The process generally refers to a chemical sample that is introduced into an ionization region as either a solid, liquid, or gas. In the ionization region, the analyte is in contact with other gases and ions that are part of the ionization region. Additional ions are produced through the collision of the analyte molecules with ions within the ionization reagent that are present in the ion source, electro-magnetic device. Inside the ion source, the ionization reagent is present in large excess compared to the analyte. Electrons and/or ions entering the source will preferentially ionize the ionization reagent. Collisions with other ionization reagent molecules will induce further ionization, creating positive and/or negative ions of the analyte. The ions are drawn into the spectrometer by either a carrier gas or focused into a beam by an electromagnet, then separated into individual beams based on the mass/charge ratio of the ions. The ion beams are separated in a mass spectrometer and collected either sequentially in a single detector or simultaneously in a set of multiple detectors to yield isotopic ratios. Highly accurate results require that sample cross-contamination be minimized.

The traditional methods for explosives detection usually involve wiping the ambient surface with a special material wipe followed by thermal desorption/gas phase ionization of the explosive compounds in the presence of an ionization reagent. However, this method is not ideal for the detection of thermally labile explosives or explosives which have low vapor pressures. Low-volatility explosives are those which release very small amounts of the explosive vapor, typically at parts per trillion levels or lower, even when heated, making it extremely difficult to detect.

The terms "desorption," "desorb" and "desorbing" as used herein refer to technology of increasing the volatility of molecules, for example target analytes, such that they can be removed (separated) from the solid. Thermal desorption is not incineration, but uses heat and a flow of inert gas to extract volatile and semi-volatile organics retained in a sample matrix or on a sorbent bed. The volatilized compounds are then either collected or thermally destroyed.

In certain embodiments, the reagents of the present invention are low volatility compounds. The terms "low volatility" and "low vapor pressure" as used herein are intended to describe compositions that do not readily evaporate or sublimate at room temperature (e.g., at about 25° C.). Typically such low volatility compositions are solids or viscous liquids and have a vapor pressure at room temperature of less than 1 Torr, or more typically less that $10^{-1}$ Torr. In some preferred embodiments, the low volatility reagents of the present invention can have a vapor pressure at room temperature of or less that $10^{-2}$ Torr or, more preferably, less that $10^{-3}$ Torr.

One new class of new ionization reagents, referred to herein as "associative reagents," can include a crown ether, a glyme, a sugar, a cryptand, or a cavitand. These compounds can be used as reagents and can form host-guest complexes with target analytes. These reagents include, but are not limited to, crown ethers (such as 12-crown-4, 15-crown-5, 16-crown-4, dibenzo 21-crown-7 or 18-crown-6), glymes (such as dimethoxyethane), sugars (such as sucrose, fructose, glucose), cryptands (such as 1,10-diaza-4,7,13,16,21,24-hexaoxabicyclo[8.8.8]hexacosane, kryptofix 222), and cavitands (such as cyclodextrin, calixarene, pillararene and cucurbituril). These compounds can be applied to the substrate material by a chemical process which can include immersion in a concentrated solution, liquid spray application, or vapor deposition. Alternatively, low volatility associative reagents can be introduced via a chemically doped swipe material.

"Crown ethers" are cyclic chemical compounds that consist of a ring containing several ether groups, e.g., oligomers of ethylene oxide or derivatives of catechol. "Glymes" are derivatives of glycol ethers, e.g., dimethyloxyethanes, and include, monoglymes, diglymes, ethylglymes and tetraglymes. "Cryptands" are bi- and polycyclic multidentate compounds capable of encapsulating various cations. "Cavitands" are also container shaped molecules having cavities to engage in host-guest chemistry with guest molecules of a complementary shape and size.

Additionally, the ionization reagents of the present invention can form a host-guest complex with a target analyte. The term "host-guest" complex as used herein generally refers to complexes that are composed of two or more molecules or ions that are held in a structural relationship, at least in part, by noncovalent bonding. The host-guest complex can be held together in unique structural relationships by forces other than those of full covalent bonds. Host-guest chemistry encompasses molecular recognition and interactions through three-dimensional structures of the molecules to transiently bind one to another. The noncovalent interaction between the ionization reagent and the target analyte can be any type of, for example, hydrogen bonding, ionic bonding, van der Waals forces and hydrophobic interactions.

The term "alkyl" or "alkyl group" means a linear or branched $C_{1-12}$ alkyl group such as methyl, ethyl, propyl, isopropyl, butyl, sec-butyl, isobutyl, tert-butyl, pentyl, isopentyl, hexyl, heptyl or octyl. A "lower alkyl" group means a linear or branched $C_{1-6}$ alkyl group such as methyl, ethyl, propyl, isopropyl, butyl, sec-butyl, isobutyl, tert-butyl, pentyl and isopentyl. The alkyl or lower alkyl group may be optionally substituted with one or more groups selected from among a halogen atom, a cyano group, a hydroxyl group, a carboxyl group, an amino group, an acyl group, a sulfo group, a phosphoryl group, a cyclic amino group, an aryl group, and an alkoxy group.

The products of the reagents of the present invention and their target analytes can be formed during desorption or on the surface of, or within a swipe material, e.g., by interactions between the analyte and the reagent prior to desorption or ionization. The swipe, also referred to as a smear, wipe or substrate material, can be made of paper, metal, fabric, cloth, fibers, glass, or synthetic material. In one embodiment, the swipe is a fabric of polyester, muslin, or cotton. The swipe can also be in different shapes and sizes depending on the type of surface to be sampled. For example, the swipe can be a two-dimensional material. The two-dimensional material can be sheet-like in construction. The material can also be in a multitude of sizes and shapes. In another example, the swipe can be a swab or other three-dimensional swipe.

The swipe can be formed of material that can be resistant to chemical degradation during testing in the approximate pH range of 0.1 through 14 to avoid reacting or decomposing. The swipe can be white in color to aid test evaluation, can be heat resistant, absorbent and/or chemically resistant at elevated temperatures and can have hydrophilic properties for wetting when using fluid reagents. The swipe can also be roughened, for example, by use of a woven material, to aid in retrieving test sample particles from the environment. The swipe can also be thick enough to resist damage such as tearing during sampling, yet not be too thick such that heating of the test sample is inhibited. The swipe thickness can be optimized to achieve rapid, and even heating through the material layer.

The swipe, such as the swab, can be affixed to the end of a holder. The swipe can be permanently or temporarily affixed to the holder for ease of manipulation, usage and sampling. The swipe can also be for a single use, such as being disposable. In an exemplary embodiment, the surface of the swipe is clean, sterile, or uncontaminated with target analytes. The swipes can also be dry, damp or wet prior to use. When the swipes are used in a damp or wet state, the swipes can be dampened with a solution, such as distilled water, alcohol, or a working strength of a multipurpose detergent.

The swipes can also sample a dry, damp or wet surface. The swipes can be of absorbent material to collect the damp or wet samples. The sample surface can also be prepped by wetting or dampening with a solution prior to sampling with the swipe. The surface can be dampened with a solution, such as distilled water, alcohol, or a working strength of a multipurpose detergent.

One or more reagents according to the invention can be deposited on, embedded in or otherwise associated with, the swipe to detect one or more target analytes. The reagent association with the swipe can be through physical entrainment, non-covalent bonds, or thermally labile covalent bonds. When multiple reagents are employed, each reagent can allow the detection of a unique target analyte. The individual target analytes can be analyzed on the swipe at predetermined times and/or temperatures or temperature ranges. Each reagent deposited on, embedded in or in association with the swipe can react to a specific target analyte.

The swipe can be substantially adapted to receive or present one or more reagents to detect one or more target analytes. The swipe can have a plurality of test regions, quadrants or lines. A different ionization reagent can be deposited on each test region, quadrant or line of the swipe, generating a unique detection area of the swipe. The entire swipe can collectively generate a unique pattern or code for a particular target analyte or class of target analytes. The test regions, quadrants or lines can be detected separately or at the same time to generate the unique pattern or code for the particular target analytes or class of target analytes.

FIG. 1 provides three schema for employing associative and/or evaporative (e.g., acid-base reactive) reagents for direct detection of an oxidizer or inorganic salt MX where an associative reagent (Scheme 1) preferentially binds the counter-ion $X^+$ of the analyte to increase availability for detection of $M^-$ in negative ionization mode, where an evaporative reagent (Scheme 2) donates a proton to the analyte forming the acid form HM as a more volatile product for ionization and detection, or a co-reagent system (Scheme 3) incorporating both an associative, A or R, and a reactive reagent, H, if needed, to form a more readily detected analyte product.

In scheme 1 of FIG. 1, dissociation of the neutral parent compound to the anionic analyte increases the abundance of ionized analyte and, therefore, increased detection sensitivity. Compounds which can be used as associative reagents can form host-guest complexes with the counter-ion of the desired analyte(s) and may include but are not limited to crown ethers, glymes, sugars (sucrose, fructose, glucose), cryptands, and cavitands. Specifically, this reagent list includes 18-crown-6, dibenzo-21-crown-7, 15-crown-5, 12-crown-4, methylacetoacetate, acetophenone, acetylac-etone, triglyme, tetraglyme, sucrose, fructose, glucose, kryptofix 222 and 4-tert-butylcalix[6]arene.

In scheme 2, formation of the acid analog of the analyte provides a new chemical product with higher vapor pressure, therefore increased availability at lower desorption temperatures, e.g. perchloric acid (7 Torr at room temperature) from potassium perchlorate (vapor pressure much less than $10^{-6}$ Torr, melting point 356° C.).

More generally, the evaporative reagents of the present invention can react with an ionic analyte by forming a conjugate that is more volatile than the target analyte species itself, e.g., by forming the conjugate acid of the analyte through an acid-base reaction, thereby increasing the vapor pressure of the analyte species and allowing the anion to be more readily available for detection in an ion detection apparatus.

In certain embodiments, the reagent compound is an acid (proton donor) which may include but is not limited water, sulfuric acid, hydrochloric acid, hydrofluoric acid, hydroiodic acid, hydrobromic acid, nitric acid, oxalic acid, hydrogen sulfate, phosphoric acid, formic acid, benzoic acid, acetic acid, propionic acid, or other organic acids of the form R—COOH where R is an alkyl, substituted alkyl, aryl, or substituted aryl group. Use of the acid reagent results in the formation of one or more ions for detection by interaction between the reagent and analyte(s).

Various other compositions can also serve as evaporative reagents, so long as they are capable of converting an analyte (or an ionic species of an analyte) into a composition having a higher vapor pressure than the analyte itself. For example, quaternary ammonium compounds, such as tetraalkylammonium hydroxide ($NR_4OH$), can serve as an evaporative agents for detection of nitrates, such as $KNO_3$, by forming more volative nitrate species, e.g., $NR_4NO_3$. The class of evaporative reagents can include alkylammonium salts, hydroxides, etc. that generate alkyl ammonium cations (N—R1-R2-R3-R4 where R1-R4 are preferably the same or different, straight or branched, lower alkyls).

With reference again to FIG. 1, scheme 3 illustrates that, for certain analytes, a co-reagent system employing both an associative reagent for the counter-ion and an evaporative reagent to donate a proton (or other cation) to the analyte in an acid-base reaction can be useful to increase detection.

EXAMPLE 1

This invention has been reduced to practice and employed to detect potassium perchlorate via API mass spectrometry. As described earlier, in negative-mode atmospheric pressure chemical ionization, the ionization efficiency is extremely limited. In order to increase the amount of free perchlorate anion available for detection, an associative reagent was added. In these experiments, a solid reagent, namely dibenzo-21-crown-7 (CAS#14098-41-0), was added to the sample solution containing potassium perchlorate at equimolar concentrations in methanol. The perchlorate anion ($^{35}ClO_4^-$) is present at m/z 99. We infused this solution into the APCI TurboV ionization source of a 4000QTrap MS (ABSCIEX) operating in negative polarity and detected the ionized perchlorate anion, $ClO_4^-$.

FIG. 2 is a single quadrupole negative mode mass spectra showing the use of an associative reagent (dibenzo 21-crown-7) to preferentially sequester the potassium counter-ion of potassium perchlorate to increase the available perchlorate anion (m/z 99 for $^{35}ClO_4^-$ and m/z 101 for $^{37}ClO_4^-$) for ionization. The detection sensitivity increased by a factor of 10 using the associative reagent.

EXAMPLE 2

Figure 3:
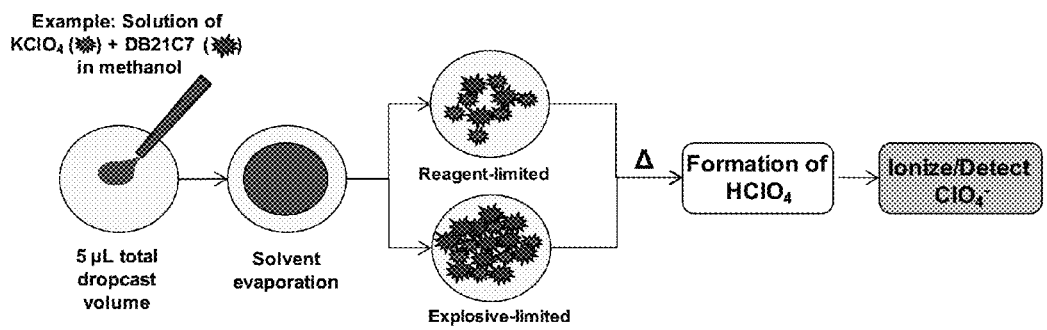
FIG. 3 is a flowchart of the TD-APCI method, including solid sample preparation, that was used to demonstrate the present invention. The process shown in FIG. 3 was used to demonstrate that the molar ratio between the reagent and the analyte determines the reaction efficiency, and by extension, the efficacy of the present invention. In cases where there is an excess of analyte (explosive), there is insufficient quantity of the reagent to react with all the explosive and the benefits of the present invention are limited. This circumstance is considered "reagent limited". In order to ensure maximum reaction of the analyte (explosive) with the reagent, an excess of reagent is needed. In this circumstance the reaction is considered "explosive limited". The preferred embodiment of this invention is to operate in the "explosive limited" regime, although some benefit is also realized in the "reagent limited" regime as well. The example shown in FIG. 3 is for potassium perchlorate and dibenzo-21-crown-7 (DB21C7) reagent generating highly volatile $HClO_4$ for detection of the $ClO_4^-$ anion.

FIG. 3 is a flowchart of the TD-APCI method, including solid sample preparation, that was used to demonstrate the present invention. The process shown in FIG. 3 was used to demonstrate that the molar ratio between the reagent and the analyte determines the reaction efficiency, and by extension, the efficacy of the present invention. In cases where there is an excess of analyte (explosive), there is insufficient quantity of the reagent to react with all the explosive and the benefits of the present invention are limited. This circumstance is considered "reagent limited". In order to ensure maximum reaction of the analyte (explosive) with the reagent, an excess of reagent is needed. In this circumstance the reaction is considered "explosive limited". The preferred embodiment of this invention is to operate in the "explosive limited" regime, although some benefit is also realized in the "reagent limited" regime as well. The example shown in FIG. 3 is for potassium perchlorate and dibenzo-21-crown-7 (DB21C7) reagent generating highly volatile $HClO_4$ for detection of the $ClO_4^-$ anion.

Figure 4:
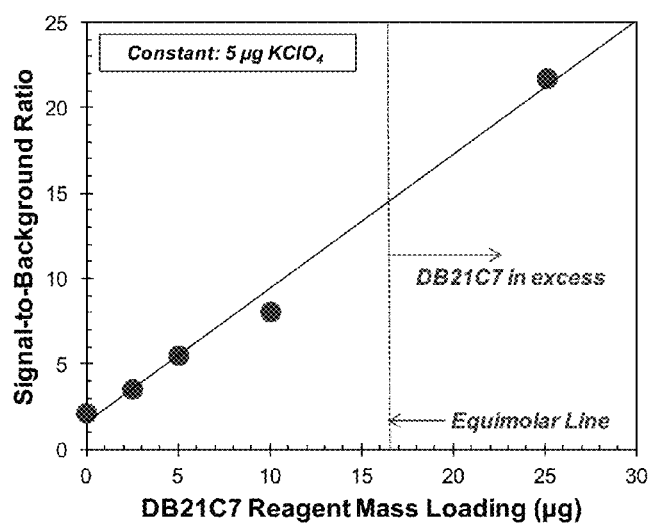
FIG. 4 is a graph showing an example for potassium perchlorate and dibenzo-21-crown-7 (DB21C7) reagent generating highly volatile $HClO_4$ for detection of the $ClO_4^-$ anion.

FIG. 4 shows results demonstrating that DB21C7 increases the signal-to-background ratio by a factor of greater the 25– for detection of $ClO_4^-$ from $KClO_4$ when the reagent is present in molar excess over the explosive.

Figure 5:
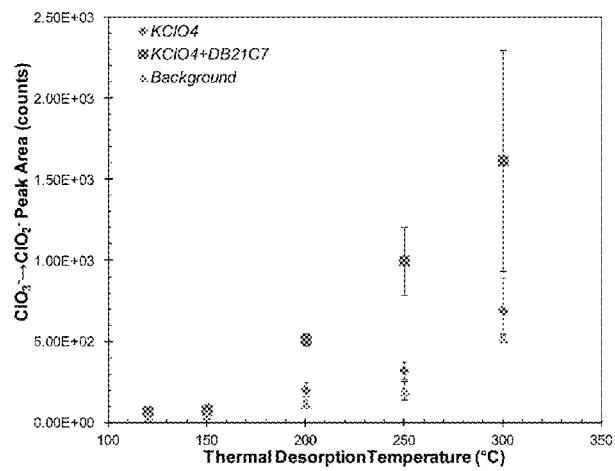
FIG. 5 is a graph of TD-APCI of potassium perchlorate ($KClO_4$) where the instrument response (peak area) is plotted as a function of thermal desorption APCI source temperature (triplicate measurements) for 5 µg $KClO_4$ (diamonds), 5 µg $KClO_4$ with 10 µg dibenzo-21-crown-7 (DB21C7) (squares), and background (clean silicon wafer substrate, triangles)

FIG. 5 is a graph of TD-APCI of potassium perchlorate ($KClO_4$) where the instrument response (peak area) is plotted as a function of thermal desorption APCI source temperature (triplicate measurements) for 5 µg $KClO_4$ (diamonds), 5 µg $KClO_4$ with 10 µg dibenzo-21-crown-7 (DB21C7) (squares), and background (clean silicon wafer substrate, triangles). This data shows the temperature effect on instrument response (reported as signal-to-background ratio) while the mass loading of the explosive and reagent remained a constant 1:2 ratio using 5 µg explosive with 10 µg reagent. One key observation from the thermal desorption study of solid explosives residues is that the thermal dependence of the signal varies by compound, thus the reagent mechanism does not take place in solution-phase at room temperature. Instead, the signal enhancement is dependent on thermal phase change properties, such as melting point and vapor pressure, which affect the mixing efficiency of available reagent with the explosive.

Figure 6:
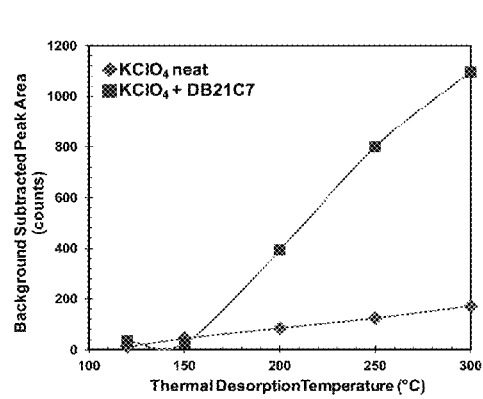
FIG. 6 is a graph showing TD-APCI-MS/MS instrument response vs thermal desorption temperature for potassium perchlorate ($KClO_4$) with and without dibenzo-21-crown-7 (DB21C7) reagent rendered as background-subtracted signal intensity determined using data in FIG. 5, comparing 5 µg $KClO_4$ (diamonds) and 5 µg $KClO_4$ with 10 µg dibenzo-21-crown-7 (DB21C7) (squares), where background is a clean silicon wafer substrate
Figure 7:
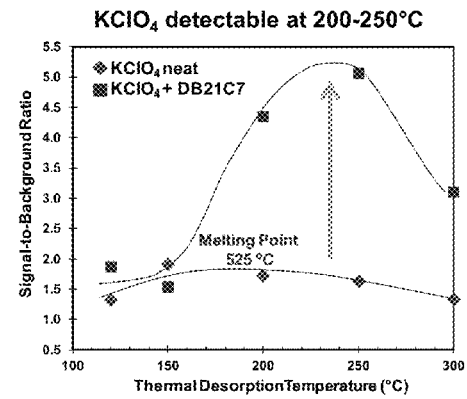
FIG. 7 is a graph showing TD-APCI-MS/MS instrument response vs thermal desorption temperature for potassium perchlorate ($KClO_4$) with and without dibenzo-21-crown-7 (DB21C7) reagent rendered as signal-to-background ratio determined using data in FIG. 5, comparing 5 µg $KClO_4$ (diamonds) and 5 µg $KClO_4$ with 10 µg dibenzo-21-crown-7 (DB21C7) (squares), where background is a clean silicon wafer substrate.

FIGS. 6 and 7 show the desorption-temperature-dependence of the MS instrument response from solid $KClO_4$ residue in the absence and presence of the crown ether reagent. Signal continues to increase for $KClO_4$ with reagent at higher temperature (300° C.) as shown in FIG. 6; however, at the expense of increasing background clutter due to chemical off-gassing from the unpassivated aluminum ionization source. Neat $KClO_4$ did not produce a signal-to-background ratio over 2, while in the presence of crown ether reagent, $KClO_4$ was detected at modest thermal desorption temperatures (200-250° C.) with a signal-to-background ratio of up to 5. Given this information, 200-250° C. is the most beneficial and practical operating temperature range for this analyte. The background will depend on instrument/source conditions, materials, and historical contamination of the instrument. The 1:2 explosive-reagent mixture is reagent-limited by molarity. Signal enhancement is expected to be at least 25× or higher under explosive-limited conditions. Greater signal enhancements are possible using even higher amounts of reagent molar excess.

EXAMPLE 3

FIG. 8-10 show the desorption-temperature-dependent relationships of the MS instrument response from solid $NaClO_4$ residue in the absence and presence of the crown ether reagent.

FIGS. 9 and 10 show TD-APCI-MS/MS instrument response versus thermal desorption temperature for sodium perchlorate ($NaClO_4$) with and without dibenzo-21-crown-7 (DB21C7) reagent rendered as both background-subtracted signal intensity (FIG. 9) and signal-to-background ratio (FIG. 10) determined using data in FIG. 8, comparing 5 µg $NaClO_4$ (blue diamonds) and 5 µg $NaClO_4$ with 10 µg dibenzo-21-crown-7 (DB21C7) (red squares), where background is a clean silicon wafer substrate.

Signal continues to increase for $NaClO_4$ with reagent at higher temperature (300° C.) as shown in the FIG. 10; however, at the expense of increasing background clutter from chemical off-gassing from the unpassivated aluminum ionization source. Neat $NaClO_4$ did not produce a signal-to-background ratio over 2, while in the presence of crown ether reagent, $NaClO_4$ was detected at modest thermal desorption temperatures (200-250° C.) with a signal-to-background ratio over 10. Given this information, 250° C. is the most beneficial and practical operating temperature range for this analyte. The background will depend on instrument/source conditions, materials, and historical contamination. The 1:2 explosive-reagent mixture is reagent-limited by molarity and signal enhancement is expected to be considerably higher under explosive-limited conditions, as shown in FIG. 8. Greater signal enhancements are possible using even higher amounts of reagent molar excess.

EXAMPLE 4

Swipe substrates with reagents according to the invention impregnated into them were also developed. Through co-vaporization of both the target analyte and the reagent into the ionization space of an instrument, the two become in communication with one another resulting in ionization of the target analyte. The ionization can result in the formation of a complex between the target analyte and the reagent with unique characteristics for detection. The complex can have detectable properties that include shifts in mass or ion mobility for increased selectivity. Also, if the target analyte was previously undetectable, formation of a complex can allow detection. In some cases, the complex will be detectable with lower background and therefore increase sensitivity.

Figure 11:
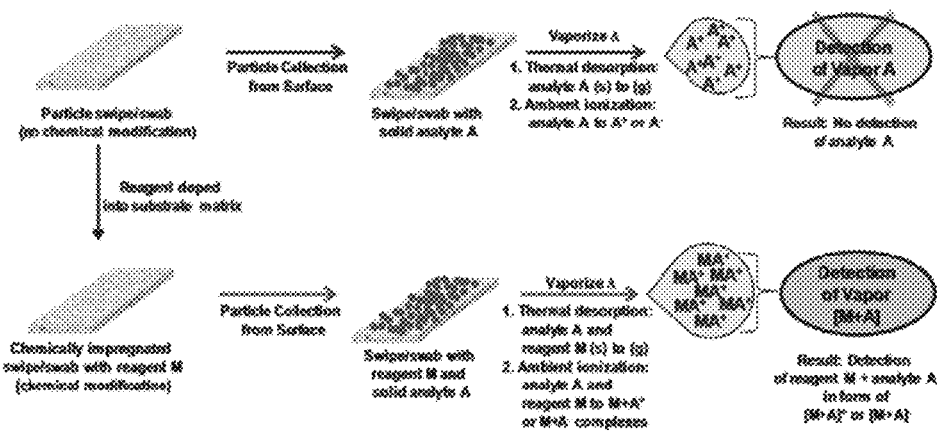
FIG. 11 illustrates the concept of doping a chemical reagent into substrate media (usually a fabric of polyester, muslin, or cotton) entraining low volatility compounds until released by desorption (e.g. thermal) and provides a flow diagram comparing a reagent impregnated swipe approach (bottom flow diagram) versus the use of swipes with no chemical modification (top flow diagram)

FIG. 11 illustrates the concept of doping a chemical reagent or ionization reagent into a substrate material or swipe (usually made of a fabric of polyester, muslin, or cotton). The substrate will entrain low volatility compounds until released by desorption (e.g. thermal). FIG. 11 also provides a flow diagram comparison of the proposed ionization reagent impregnated swipe approach versus the use of current swipes with no chemical modification. The example shown is for chemical sensors with sample introduction via thermal desorption and detection of the ionized reagent+target analyte adduct in either positive or negative ion mode.

The chemicals used in conventional ambient ionization sources are introduced within the detection system as a vapor reagent in the carrier gas. This limits the list of reagents to high vapor pressure and/or lower molecular weight candidates. Low volatility compounds often provide higher affinity to the desired target analyte and increase probability of detection not achieved with higher volatility reagents. In addition, reagents can be used that are not otherwise amenable to entrainment in a carrier gas, thus making accessible a wider range of ionization reagents, including those of high molecular weight. One advantage of high molecular weight (>400 Da) reagents is that can possess more complex molecular structures and thus they can act as better ionization (or associative, evaporative, adductive or redox) reagents. These high molecular weight reagents are solids at room temperature and cannot be easily or reliably delivered as a vapor in a carrier gas. However, by virtue of their high molecular weight, they can form high-molecular adducts or complexes with the target analyte making detection much easier.

Ammonium nitrate residues were detected via API mass spectrometry using regent-impregnated swipes. Ammonium ($NH_4^+$) was present at m/z 18, however, this was below the low mass cutoff of many mass spectrometers. In order to detect ionized $NH_4^+$ liberated by thermal desorption, a conventional thermal desorption swipe was chemically-modified to incorporate a crown ether reagent known to adduct $NH_4^+$. The ionization reagent yielded a higher molecular weight complex that was ionizable via atmospheric-pressure chemical ionization.

In these experiments, a solid reagent, either dibenzo-21-crown-7 (CAS#14098-41-0) or 18-crown-6 (CAS#17455-13-9), was entrained into the fabric of either muslin, cotton or polyester swipes. This swipe doping procedure consisted of drop-casting a known volume of a concentrated crown ether stock solution in acetonitrile onto the swipe material. The volatile solvent was allowed to dry at room temperature leaving the low vapor pressure crown ether in solid-state within the swipe matrix. The reagent-impregnated swipe was then used to swipe a known mass of solid ammonium nitrate residue from a Teflon surface. The contaminated swipe was placed on a thermal desorption stage which was pre-heated to 200° C. Ambient ionization mass spectrometry (specifically the Direct Analysis in Real Time® ionization source (JEOL/Ionsense) coupled with a 4000QTrap MS (ABSCIEX) operating in positive polarity was used to ionize the desorbed product and detect the ionized crown ether reagent+$NH_4^+$ complex. This experiment was performed in open atmosphere which contained levels of ambient ammonia and produced $NH_4^+$ upon positive ionization. Given the crown ether's high affinity for $NH_4^+$, ambient ammonia contributed to an elevated background in the mass channel for the reagent+$NH_4^+$.

In these experiments, isotopically-labeled $^{15}NH_4^{15}NO_3$ which shifts the reagent+$^{15}NH_4^+$ complex (M+19) to one higher mass unit than the product created by reagent+ambient $NH_4^+$ (M+18) was utilized. Nitrogen gas was used to purged or displace the air, however, the experiment was not performed in a hermetically sealed chamber.

Figure 12:
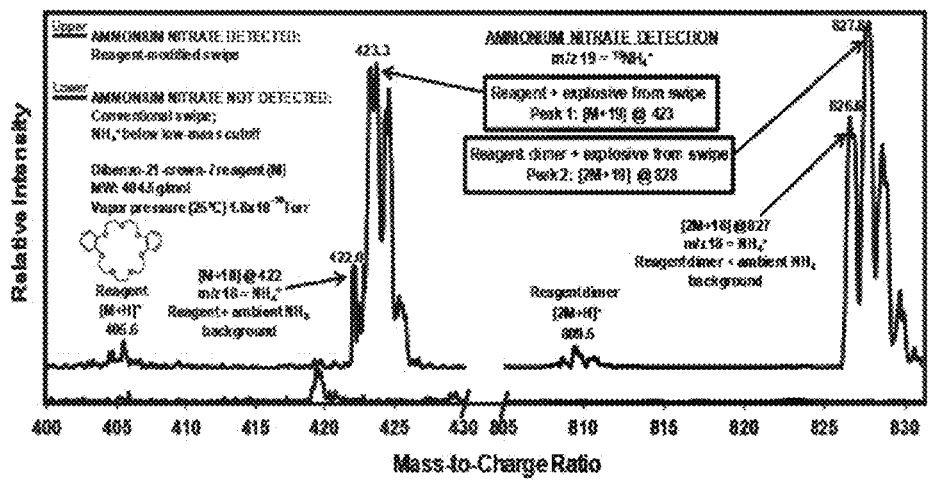
FIG. 12 is an overlay of two positive-mode mass spectra showing lack of detection of ammonium nitrate residue thermally-desorbed from a non-impregnated swipe (lower line) and detection of ammonium nitrate residue thermally-desorbed from the polyester swipe impregnated with dibenzo-21-crown-7 reagent M (upper line)

FIG. 12 is an overlay of two positive-mode mass spectra showing detection of ammonium nitrate residue thermally-desorbed from the polyester swipe impregnated with dibenzo-21-crown-7 reagent M. Without the impregnated swipe (lower line), a conventional swipe would not provide detection of ammonium above the low mass cutoff of many mass spectrometer systems. With the impregnated swipe (upper line), a swipe modified with an ionization reagent provides detection of ammonium indicating presence of the explosive. The single quadrupole mass spectrum scan shows detection of the reagent+$^{15}NH_4^+$ adducts at m/z 828 (2M+$^{15}NH_4^+$) and m/z 423 (M+$^{15}NH_4^+$). Free protonated reagent resides at m/z 405.6 (monomer) and 809.5 (dimer). Although the x axis (mass-to-charge) was magnified to visualize the higher mass region, the conventional swipe is devoid of ammonium-related peaks above the low mass threshold (~m/z 45) of this instrument. Peak intensities in the presence of ammonium residue versus a control swipe (reagent impregnated swipe without $^{15}NH_4^+$) at m/z 423 was S/N>3 and at m/z 828 was S/N>500. The same experiments with 18-crown-6 and $^{15}NH_4^{15}NO_3$ were performed and produced similar data with reagent+$^{15}NH_4^+$ adducts detected at m/z 547 (2M+$^{15}NH_4^+$) and m/z 283 (M+$^{15}NH_4^+$).

EXAMPLE 5

Figure 13:
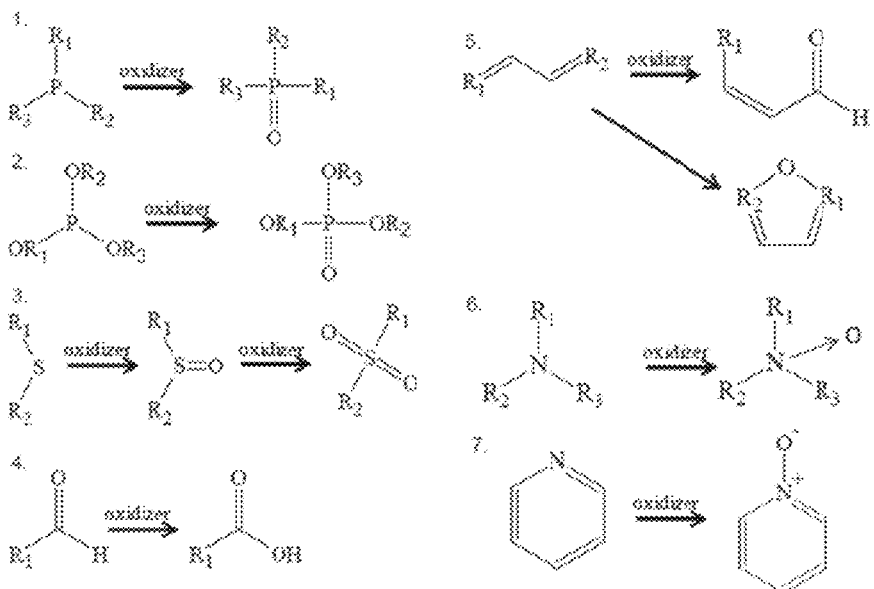
FIG. 13 illustrates general classes of reducing agents for use in the indirect detection of analytes that are strong oxidizers.

FIG. 13 illustrates a number of general classes of reducing agents for use as oxidizer ionization reagents. The chemical reaction between the reducing agent and the oxidizer are called reduction-oxidation (redox) reactions. In these reactions, the reduction potential, or potential to gain electrons, is higher for the reducing agent than the analyte, thus the final product is the reducing agent with additional oxygen atom(s). These classes of reagents include: 1) phosphines; 2) phosphites; 3) sulfides and sulfoxides; 4) aldehydes; 5) dienes; 6) amines; 7) heterocycles. Specifically, this reagent list includes but is not limited to trimethylphosphine, triphenylphosphine, trimethylphosphite, trimethylphosphite, thiophene, thiophene-1-oxide, dimethylsulfoxide, sulfoxide, vanillin, butadiene, and ethanolamine. Each R group in FIG. 13 is an atom or side chain selected independently from the groups including but not limited to hydrogen, straight or branched chain alkyl, straight or branched chain alkenyl, aryl, heteroaryl, heterocycle, and carbocycle.

The reducing agents, or reactive ionization reagents, produce an indirect technique for detecting oxidizers. For example, the reaction of hydrogen peroxide ($H_2O_2$) with 4-nitrophenyl boronic acid to form the new chemical product, 4-nitrophenol, provides a means of indirect detection of the peroxide. The data below is a demonstration of utilizing such a reagent in hydrogen peroxide detection via APCI-MS. The reaction of hydrogen peroxide with 4-nitrophenylboronic acid is simple way to measure concentration of hydrogen peroxide as it stoichiometrically converts 4-nitrophenylboronic acid into 4-nitrophenol, as shown below.

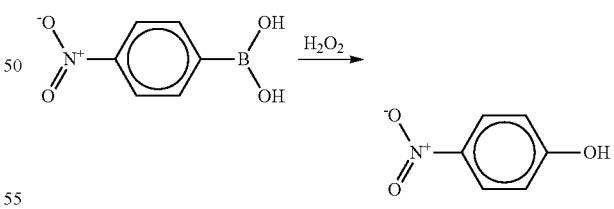

We adapted this reaction for APCI-MS and MS/MS to indirectly detect hydrogen peroxide using 4-nitrophenylboronic acid as a reactive reagent. The sensitivity of this technique will be limited by the background signal of the oxidation product. The 4-nitrophenol oxidation product (m/z 138) was observed in the MS scan of the reagent itself, 4-nitrophenylboronic acid, and may result from two potential sources. The reagent may oxidize during manufacturing, storage, or during APCI in which $O_2^-$ species are present. This indirect means of detection is attractive given the low mass of hydrogen peroxide and its highly reactive nature.

Practical field use of reactive reagents with high oxidation potential is expected to be limited given their tendency to oxidize through the fundamental APCI mechanism.

Figure 14:
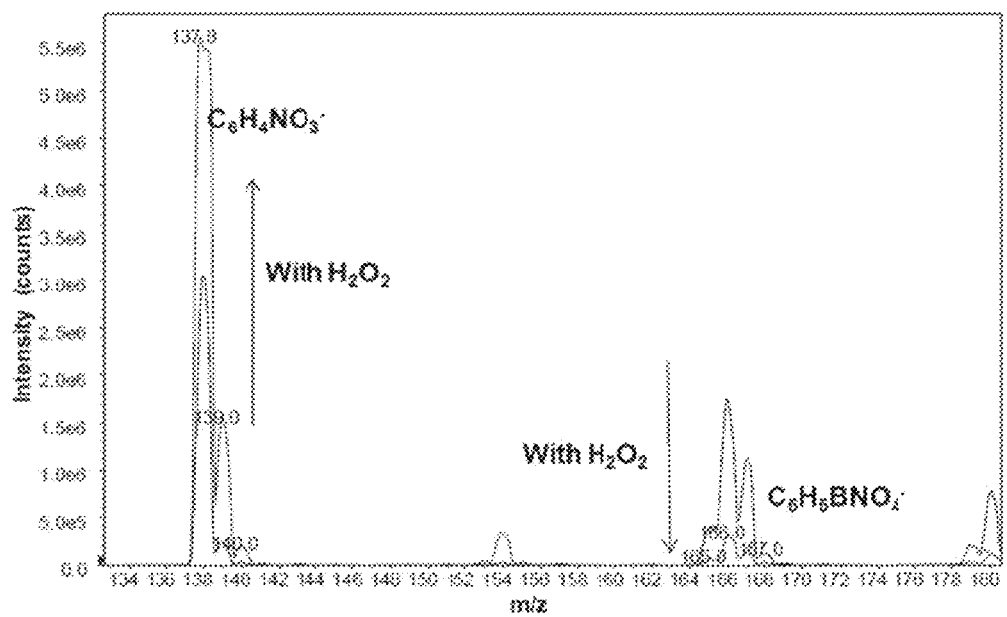
FIG. 14 is a negative mode APCI MS Q1 scan for 4-nitrophenylboronic acid in 50/50 methanol-water (solid) and 4-nitrophenylboronic acid with hydrogen peroxide in 50/50 methanol-water (crossed)

FIG. 14 shows the negative-mode single quadrupole scan of 100 μM 4-nitrophenylboronic acid overlaid with 100 μM 4-nitrophenylboronic acid with 37 μM hydrogen peroxide (1.25%) prepared in 50/50 methanol-water. Deprotonated 4-nitrophenylboronic acid at m/z of 166 and the deprotonated 4-nitrophenol peak at m/z 138 are observed.

Upon addition of hydrogen peroxide, the 4-nitrophenylboronic acid signal clearly decreased while that of the oxidation product, 4-nitrophenol, increased. To confirm these observations, we analyzed samples containing 100 μM 4-nitrophenylboronic acid in 50/50 methanol-water with varied concentration of hydrogen peroxide. Concentration of hydrogen peroxide was varied from 0.1 to 7353 μM (0.00025-25%). Blanks consisted of 100 μM 4-nitrophenylboronic acid. Samples were analyzed by direct infusion negative mode APCI. MS/MS transitions were monitored for both 4-nitrophenylboronic acid via m/z 166→>46 ($C_6H_5BNO_4^-$ to $NO_2^-$) and 4-nitrophenol via m/z 138→92 ($C_6H_4NO_3^-$ to $C_6H_4O^-$).

Figure 15:
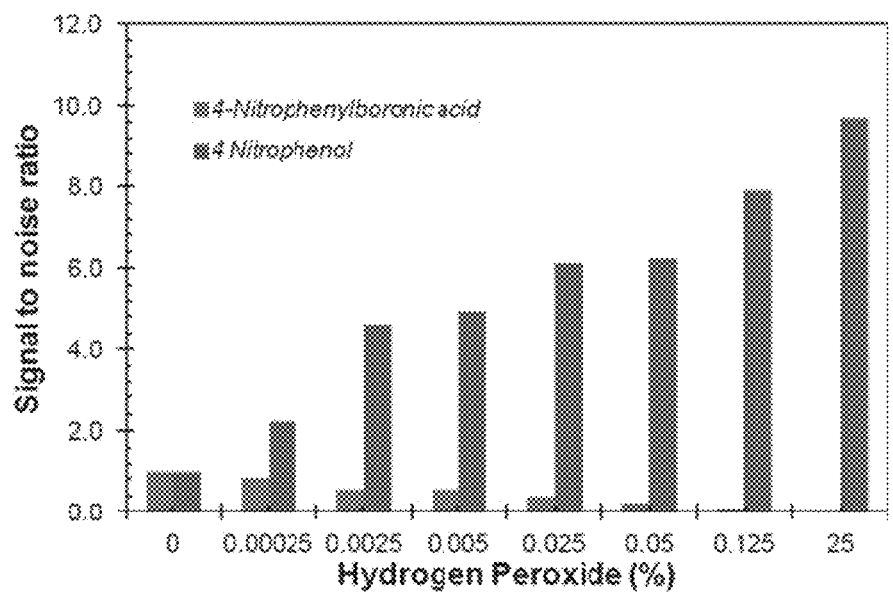
FIG. 15 illustrates the signal-to-background ratio calculated for indirect detection of hydrogen peroxide in negative mode MS/MS by the signal decrease of 4-nitrophenylboronic acid monitored by m/z 166→46 ($C_6H_5BNO_4^-$ to $NO_2^-$) and the signal increase of 4-nitrophenol monitored by m/z 138→92 ($C_6H_4NO_3^-$ to $C_6H_4O^-$) plotted as a function of hydrogen peroxide concentration.

To evaluate the practical application for indirect detection of hydrogen peroxide as an oxidation product of 4-nitrophenylboronic acid, we calculated a signal-to-background ratio for the peak areas of the sample containing hydrogen peroxide to the blank containing only 100 μM 4-nitrophenylboronic acid. Results of the MS/MS analysis are presented in FIG. 15. Monitoring the signal increase resulting from 4-nitrophenol produced by hydrogen peroxide oxidation of 4-nitrophenylboronic acid can provide a mechanism for detection of hydrogen peroxide over wide range of $H_2O_2$ concentrations (0.0025-25% v/v). Selectivity of this detection can be improved by monitoring two detection channels in MS/MS mode including signal decrease from consumption of the 4-nitrophenylboronic acid reagent and signal increase for generation of 4-nitrophenol.

One skilled in the art will appreciate further features and advantages of the invention based on the above-described embodiments. Accordingly, the invention is not to be limited by what has been particularly shown and described, except as indicated by the appended claims. All patents, publications and references cited herein (including the following listed references) are expressly incorporated herein by reference in their entirety.

What is claimed is:

1. A method for direct detection of an oxidizer analyte molecule, M potentially present in a sample as an ionizable compound or complex, MX, capable of dissociating into constituent ionic species, M⁻ and counter-ions X⁺, the method comprising:
   introducing a reagent, A, to sequester at least some of the counter-ions X⁺, as a compound or complex XA, thereby ensuring greater availability of the ionized analyte, M⁻, for detection; and
   subjecting the ionized components of the sample to mass spectrometry, whereby the presence of M in the sample can be deduced by spectrometric detection of the constituent ionic species M⁻ of the analyte.

2. The method of claim 1 wherein the method further comprises step of volatizing MX if present in the sample and dissociating it into constituent ionic species, M⁻ and counter-ions X⁺.

3. The method of claim 1 wherein the step of subjecting ionized components of the sample to mass spectrometry further comprises subjecting the ionized components to ion mobility spectrometry.

4. The method of claim 1 wherein the method further comprises associating the reagent with a swipe prior to sample collection and then using the swipe to obtain a sample.

5. The method of claim 4, wherein the reagent interacts with the analyte if present in the sample either prior to desorption in a detection instrument or after it is released into a carrier gas along with any target analyte molecules captured by the swipe following desorption.

6. The method of claim 4 wherein the reagent is either physically entrained in the swipe, bound to the swipe via non-covalent chemical bonds, or bound to the swipe via thermally labile covalent bonds.

7. The method of claim 1, wherein the reagent comprises at least one of β-keto esters, crown ethers, glymes, sugars, cryptands, amides, amines, chlorinated alkanes, organic bases, ionic dyes, and cavitands.

8. The method of claim 7 wherein the reagent comprises a crown ether selected from the group of 12-crown-4, 15-crown-5, 16-crown-4, dibenzo 21-crown-7 and 18-crown-6.

9. The method of claim 7 wherein the reagent comprises a dibenzo-21-crown-7 ether (CAS#14098-41-0).

10. The method of claim 7 wherein the reagent comprises a cryptand selected from the group of 1,10-diaza-4,7,13,16,21,24-hexaoxabicyclo[8.8.8] hexacosane and kryptofix 222.

11. The method of claim 7 wherein the reagent comprises a cavitand selected from the group of cyclodextrin, calixarene, pillararene and cucurbituril.

12. The method of claim 7 wherein the reagent comprises a sugar selected from the group of sucrose, fructose and glucose.

13. The method of claim 7 wherein the reagent comprises dimethoxyethane.

14. The method of claim 1 wherein the analyte comprises a salt of a nitrate, nitrite, chlorate, perchlorate, permanganate, dichromate or osmium tetraoxide.

15. The method of claim 1 wherein the analyte comprises a salt of a perchlorate.

16. The method of claim 1 wherein the method comprises introducing a second reagent to increase the vapor pressure of the analyte species.

17. The method of claim 16 wherein the method further comprises introducing the second reagent to form an analog of the analyte by proton or cation donation.

18. The method of claim 16 wherein the method further comprises introducing the second reagent so that an analyte anion is more readily available for detection in an ion detection apparatus.

19. The method of claim 16, wherein the second reagent comprises at least one reagent selected from the group of sulfuric acid, hydrochloric acid, hydrofluoric acid, hydroiodic acid, hydrobromic acid, nitric acid, oxalic acid, water, hydrogen sulfate, phosphoric acid, formic acid, benzoic acid, acetic acid, propionic acid, or other organic acids of the form R—COOH where R is an alkyl, substituted alkyl, aryl, or substituted aryl group or an alkyl ammonium compound.

20. The method of claim 16, wherein the second reagent is introduced to the sample separately from the first reagent.

* * * * *